US00PP32903P2

(12) United States Plant Patent
Meilland

(10) Patent No.: US PP32,903 P2
(45) Date of Patent: Mar. 23, 2021

(54) BEDDING ROSE PLANT NAMED 'MEIDYCEUS'

(50) Latin Name: *Rosa hybrida*
Varietal Denomination: MEIDYCEUS

(71) Applicant: The Conard-Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 16/602,903

(22) Filed: Dec. 23, 2019

(30) Foreign Application Priority Data

Sep. 24, 2019 (QZ) ..... 2019/2397

(51) Int. Cl.
*A01H 5/02* (2018.01)
*A01H 6/74* (2018.01)

(52) U.S. Cl.
USPC ..... Plt./103

(58) Field of Classification Search
USPC ..... Plt./103, 133, 144
CPC ..... A01H 5/02; A01H 5/0222; A01H 5/10; A01H 5/00; A01H 6/74; A01H 6/749
See application file for complete search history.

(56) References Cited

PUBLICATIONS

Societe Nationale d'Horticulture de France, Results of the 89th International New Roses Competition in Lyon—2019 Competition, retrieved on Jun. 24, 2020, retrieved from the Internet at https://www.snhf.org/actualites/page/5/, pp. 1, 49-56. (Year: 2019).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of bedding rose plant, herein referred to by its cultivar name, 'MEIDYCEUS', is provided which forms on a nearly continuous basis attractive, cup shaped, very pure white double flowers. Attractive, glossy foliage is formed, which contrasts beautifully with the blossoms. A bushy growth habit is displayed. The disease tolerance is very good, particularly against black spot and *Oidium*. The new variety is well suited for providing attractive ornamentation in the landscape.

1 Drawing Sheet

Botanical/commercial classification:
Latin name: *Rosa hybrida.*
Varietal denomination: 'MEIDYCEUS'.

CROSS-REFERENCE TO RELATED APPLICATIONS

This application claims priority to Plant Breeders' Right Application Number 2019/2397, which was filed at Community Plant Variety Office in the European Union on Sep. 24, 2019, the contents of which are hereby incorporated by reference for all purposes.

SUMMARY OF THE INVENTION

The new variety of *Rosa hybrida* plant was created by artificial pollination wherein two parents were crossed which previously had been studied in the hope that they would contribute the desired characteristics. The female parent (i.e., the seed parent) was the 'THE FAIRY' variety (non-patented). The male parent (i.e., the pollen parent) was the 'AUSMAS' variety (non-patented).

The parentage of the new variety can be summarized as follows:

'THE FAIRY' x 'AUSMAS'

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms attractive, cup shaped, very pure white double flowers,
(b) forms attractive, glossy foliage, and
(c) exhibits good resistance to diseases, particularly against black spot and *Oidium.*

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'THE FAIRY' variety (i.e., the seed parent) displays pink colored blossoms and the 'AUSMAS' variety (i.e., the pollen parent) displays yellow colored blossoms, whereas the new variety displays very pure white colored flowers. Moreover, the new variety can be readily distinguished from other similar non-parental varieties. For example, the 'Meiradena' variety (U.S. Plant Pat. No. 26,790) displays less petals and a less pure white flower color compared to the new variety.

The new variety has been found to undergo asexual propagation in Le Cannet des Maures, Var, France by a number of routes, including softwood cuttings and grafting t-bud. Asexual propagation by the above-mentioned techniques in Le Cannet des Maures, Var, France has shown that the characteristics of the new variety are stable and are strictly transmissible by such asexual propagation from one generation to another. Accordingly, the new variety undergoes asexual propagation in a true-to-type manner.

The new variety has been named 'MEIDYCEUS'.

The first offer for sale of the new variety was Mar. 31, 2019 in France by the inventor or another who obtained the new variety directly or indirectly from the inventor.

BRIEF DESCRIPTION OF THE PHOTOGRAPH

The accompanying photograph of FIG. 1 shows as nearly true as it is reasonably possible to make the same, in a color illustration of this character, typical specimens of the plant parts of the new variety. The rose plants of the new variety were approximately two years of age and were observed during July while budded on *Rosa Laxa* and growing outdoors at Le Cannet des Maures, Var, France. Dimensions in centimeters are indicated at the bottom of FIG. 1.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—under surface.

Element 14—illustrates a specimen of a leaf with 5 leaflets—plan view—under surface.

Element 15—illustrates a specimen of a leaf with 3 leaflets—plan view—upper surface.

Element 15—illustrates a specimen of a leaf with 5 leaflets—plan view—upper surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of two-year-old specimens of the new variety during July while budded on *Rosa Laxa* and growing outdoors at Le Cannet des Maures, Var, France.

Commercial classification: Bedding Rose Plant.

Plant:

*Habit*.—Bushy.

*Height*.—Typically 60 cm to 80 cm on average.

*Width*.—Typically 60 cm to 80 cm on average.

Branches:

*Color*.—Young stems: commonly near Yellow-Green Group 146B. — adult wood: commonly near Yellow-Green Group 146B.

*Length of main stem*.—Typically 30 cm to 40 cm on average.

*Young shoots*.—Anthocyanin coloration: medium/weak intensity and only on the reverse side of the foliage and on the petiole rachis, commonly near Greyed-Red Group 178A.

*Thorns*.—Configuration on adult stems: upright and elongated on the upper surface and slightly concave on the under surface. — long prickles — quantity: commonly approximately 6 thorns per 10 cm long young stem and commonly 6 thorns per 10 cm long adult stem. — long prickles — base shape: oval. — long prickles — size: approximately 1.1 cm in length on average on young stems and approximately 1.0 cm on adult stems. — long prickles — color commonly near Greyed-Orange Group 164B on young stems and commonly near Greyed-Orange Group 166C on adult stems. — small prickles (<1.0 cm) — quantity: commonly absent.

Foliage:

*General appearance*.—Dense with a glossy aspect.

*Number of leaflets*.—3, 5, and 7; most often 5 or 7.

*Terminal leaflet*.—Length: approximately 5.5 cm on average. — width: approximately 3.4 cm on average.

*Entire leaf*.—Length: approximately 9.5 cm on average. — width: approximately 5.5 cm on average.

*New foliage*.—Upper surface color: commonly near Yellow-Green Group 146B. — under surface color: commonly near Yellow-Green Group 146C. — anthocyanin coloration: absent.

*Adult foliage*.—Upper surface color: commonly near Yellow-Green Group 147A. — under surface color: commonly near Yellow-Green Group 147B. — anthocyanin coloration: absent.

Leaflets:

*Shape*.—Tip: acuminate. — base: obtuse.

*Glossiness of upper surface*.—Medium intensity.

*Texture*.—Leathery.

*General appearance*.—Oval.

*Edge*.—Slightly denticulate.

*Serration*.—Small and single.

*Undulation on the margin*.—Medium.

*Petiole rachis*.—Color of upper surface: commonly near Yellow-Green Group 148B. — color of under surface: commonly near Yellow-Green Group 148A. — prickles: few in amount, small size, color is commonly near Yellow-Green Group 148A.

*Petioles*.—Upper surface: no glandular. — under surface: few prickles. — color of upper surface: commonly near Yellow-Green Group 148A. — color of under surface: commonly near Yellow-Green Group 148B. — petiole length of terminal leaflet: approximately 2.4 cm on average.

*Stipules*.—General appearance: adnate, pectinate and narrow. — length: approximately 1.7 cm on average. — width: approximately 0.7 cm on average. — color of upper surface: commonly near Yellow-Green Group 148B. — color of under surface: commonly near Yellow-Green Group 148A.

Inflorescence:

*Number of flowers per stem*.—Generally between 3 to 15 flowers per stem.

*Lastingness of the bloom*.—Cut flower: approximately 4 days on average. — on the plant: approximately 12 days on average.

*Bud*.—Shape: conical. — size: medium. — length: approximately 2.1 cm on average. — width: approximately 1.7 cm on average. — color as calyx breaks: — upper surface: commonly near White Group 155B. — under surface: commonly near White Group 155B.

*Sepals*.—Length: approximately 1.5 cm on average. — width: approximately 0.7 cm on average. — shape: — at the top: narrow and longish. — at the base: upright. — extensions: weak. — upper surface: — texture: tomentous. — color: commonly near Yellow-Green Group 148C. — under surface: — texture: smooth. — color: commonly near Yellow-Green Group 146C.

*Receptacle*.—Color: commonly near Yellow-Green Group 146C. — length: approximately 0.6 cm on average. — width: approximately 0.5 cm on average. — surface: smooth. — shape: funnel shaped.

*Peduncle*.—Length: approximately 4.1 cm on average. — width: approximately 0.2 cm on average. — surface: pubescent. — color: commonly near Yellow-Green Group 146C.

*Flower*.—Average size when fully open: commonly between 5.0 to 7.0 cm on average. — depth: typically 3.0 cm to 4.0 cm on average. — shape: cup shaped, round when viewed from the top. — number of petals under normal conditions: approximately 55 to 63 petals on average. — shape of the petal: external petals are rounded; internal petals are egg shaped. — base: obtuse. — top: rounded. — petal margin: smooth. — texture of the petal: leathery. — petal length: approximately 3.7 cm on average. — petal width: approximately 3.0 cm on average. — petal arrangement: imbricated without petaloids. — petal drop: petals drop off cleanly before drying. — fragrance: none. color when opening: spot at the base: absent. — upper surface of the flower: commonly near White Group 155B. — under surface of the flower: commonly near White Group 155B. — color of the open flower: — spot at the base: absent. — upper surface of the flower: commonly near White Group 155B. — under surface of the flower: commonly near White Group 155B. — anthers: number is approximately 103 on average, length is approximately 0.1 cm on average, coloration is commonly near Yellow-Orange Group 21B, and arrangement is regular around styles. — filaments: length is approximately 0.3 cm on average and coloration is commonly near Yellow-Orange Group 20A. — styles: length is approximately 0.1 cm on average, coloration is commonly near Yellow Group 3C, and number is approximately 71 on average. — stigmas: size is approximately 0.2 cm on average and coloration is commonly near Yellow Group 3D. — pollen: not available at this stage. — hips: not available at this stage.

Development:

*Vegetation*.—Strong.

*Blooming*.—Early in the season, very abundant and nearly continuous, typical from May to October in France.

*USDA hardiness zone*.—Zone 5.

*Tolerance to disease*.—Very good, and particularly against black spot (*Diplocarpon rosae*) and powdery mildew (*Oidium*).

The new 'MEIDYCEUS' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant characterized by the following combination of characteristics:

(a) forms attractive, cup shaped, very pure white double flowers, (b) forms attractive, glossy foliage, and (c) exhibits good resistance to diseases, particularly against black spot and *Oidium;* substantially as herein shown and described.

* * * * *

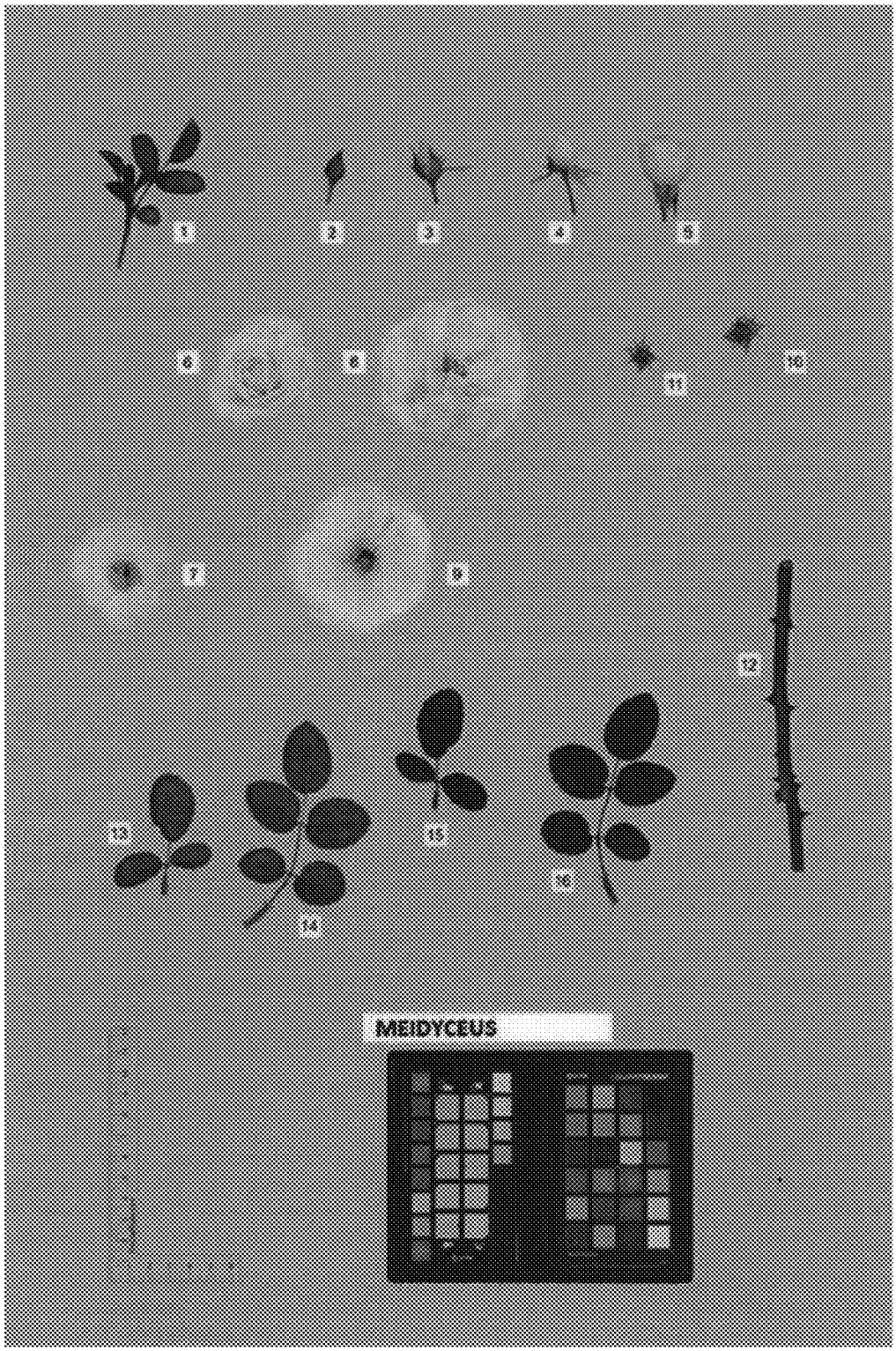
MEIDYCEUS